United States Patent
Wu et al.

(10) Patent No.: US 9,668,497 B2
(45) Date of Patent: *Jun. 6, 2017

(54) FLAVOR-ENHANCING COMPOUNDS

(71) Applicant: INTERNATIONAL FLAVORS & FRAGRANCES INC., New York, NY (US)

(72) Inventors: Hou Wu, East Brunswick, NJ (US); Thumpalasseril V. John, Morganville, NJ (US); Xiaoqing Tang, Holmdel, NJ (US); Jung-A Kim, Edgewater, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/865,203

(22) Filed: Sep. 25, 2015

(65) Prior Publication Data

US 2017/0086476 A1   Mar. 30, 2017

(51) Int. Cl.
| | |
|---|---|
| *A23G 4/06* | (2006.01) |
| *A61K 8/34* | (2006.01) |
| *A61K 8/49* | (2006.01) |
| *A61Q 11/00* | (2006.01) |
| *A23L 1/22* | (2006.01) |
| *A23L 1/226* | (2006.01) |

(52) U.S. Cl.
CPC ............ *A23G 4/06* (2013.01); *A23L 1/22091* (2013.01); *A23L 1/22664* (2013.01); *A61K 8/34* (2013.01); *A61K 8/498* (2013.01); *A61Q 11/00* (2013.01); *A23V 2002/00* (2013.01); *A61K 2800/40* (2013.01)

(58) Field of Classification Search
None
See application file for complete search history.

(56) References Cited

FOREIGN PATENT DOCUMENTS

| | | | | |
|---|---|---|---|---|
| EP | 2606746 A1 | * | 6/2013 | ......... A23L 1/22091 |
| JP | 2002255778 A | * | 9/2002 | |

OTHER PUBLICATIONS

Renessenz ([retrieved from on-line website http://www.renessenz.com/products/content/winsense-ws-5, last visit date:Aug. 2, 2016]).*
Machine Translation of JP2002-255778, obtained from EPO machine translation on Aug. 8, 2016.*
Pubchem, "7,8-dihydroxyflavone" ([retrieved from on-line website: https://pubchem.ncbi.nlm.nih.gov/compound/7_8-dihydroxyflavone#section=Top, last visit date: Aug. 9, 2016]).*
Andero, R., et al., "Fear Extinction and BDNF: Translating Animal Models of PTSD to the Clinic", Genes, Brain and Behavior (2012), vol. 11, pp. 503-512, (doi: 10.1111/j.1601-183X.2012.00801.x).
Chan, C. B., et al., "Activation of Muscular TrkB by its Small Molecular Agonist 7,8-Dihydroxyflavone Sex-Dependently Regulates Energy Metabolism in Diet-Induced Obese Mice", Chemistry and Biology, vol. 22, pp. 355-368, (Mar. 19, 2015), Elsevier Ltd.
Colombo, P.S., et al., "Farinose Alpine Primula Species: Phytochemical and Morphological Investigations", Phytochemistry, vol. 98, (2014) pp. 151-159.
Kitazaki, H., et al., "Separation and Recovery of Flavonoids by Means of Solvent Extraction and Adsorption on Solvent-Impregnated Resin", ISEC '96, Melbourne Australia, 1667-1672.

* cited by examiner

*Primary Examiner* — Ernst V Arnold
*Assistant Examiner* — Kyung Sook Chang
(74) *Attorney, Agent, or Firm* — Martin Zhang; XuFan Tseng; Elizabeth M. Stover

(57) ABSTRACT

The present invention has discovered that 7,8-dihydroxy-2-phenyl-4H-chromen-4-one and a salt thereof have unexpected and advantageous cooling enhancement and modification properties. Thus, a composition comprising a cooling compound and an effective amount of 7,8-dihydroxy-2-phenyl-4H-chromen-4-one can be used to enhance or modify the cooling sensation in the mouth, in the nasal cavity and/or on the skin, and can also augment, enhance or impart a cooling sensation to products such as foodstuff, chewing gums, dental or oral hygiene products, topical products, nasal care products and toilet articles.

11 Claims, No Drawings

FLAVOR-ENHANCING COMPOUNDS

FIELD OF THE INVENTION

The present invention relates to the use of 7,8-dihydroxy-2-phenyl-4H-chromen-4-one and a salt thereof to enhance or modify the cooling sensation in various topical and ingestible products, such as foodstuff, chewing gums, dental or oral hygiene products, topical products, nasal care products and toilet articles.

BACKGROUND OF THE INVENTION

A large number of compounds are known to provide a cooling sensation in the mouth, in the nasal cavity and/or on the skin. The best known and most widely used of these is menthol, which, in addition to olfaction, causes a cooling response on cold receptors in the oral cavity, the nasal cavity and on the skin. Unfortunately, menthol also exhibits some undesirable properties, such as a strong mint smell, a bitter taste and relatively high volatility. There still remains a need for novel coolant compositions that provide strong and substantive refreshing and cooling attributes in the absence of negative aroma, negative taste and negative cooling attributes.

Thus, despite the previous disclosure in the art, there is an ongoing need for novel compounds that enhance or modify the cooling sensation in the mouth, in the nasal cavity and/or on the skin, preferably by lowering the levels of cooling compounds such as menthol in topical and ingestible compositions to provide advantageous properties as well as economy of use.

SUMMARY OF THE INVENTION

The present invention has discovered that 7,8-dihydroxy-2-phenyl-4H-chromen-4-one represented by Formula I set forth below has unexpected and advantageous cooling enhancement and modification properties:

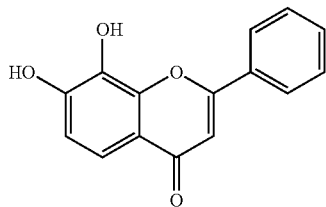

Formula I

One embodiment of the invention relates to a composition comprising a cooling compound and an effective amount of 7,8-dihydroxy-2-phenyl-4H-chromen-4-one or a salt thereof.

Another embodiment of the invention relates to a process of augmenting, enhancing or imparting a cooling sensation to a product selected from the group consisting of a foodstuff, a chewing gum, a dental or oral hygiene product, a topical product, a nasal care product and a toilet article comprising the step of incorporating a cooling compound and an effective amount of 7,8-dihydroxy-2-phenyl-4H-chromen-4-one or a salt thereof.

Another embodiment of the invention relates to a process of providing a cooling sensation in the mouth, in the nasal cavity and/or on the skin comprising the step of incorporating a cooling compound and an effective amount of 7,8-dihydroxy-2-phenyl-4H-chromen-4-one or a salt thereof.

Another embodiment of the invention relates to a product selected from the group consisting of a foodstuff, a chewing gum, a dental or oral hygiene product, a topical product, a nasal care product and a toilet article comprising a cooling compound and an effective amount of 7,8-dihydroxy-2-phenyl-4H-chromen-4-one or a salt thereof.

Another embodiment of the invention relates to a composition comprising menthol and an effective amount of 7,8-dihydroxy-2-phenyl-4H-chromen-4-one or a salt thereof.

Another embodiment of the invention relates to a process of augmenting, enhancing or imparting a cooling sensation to a product selected from the group consisting of a foodstuff, a chewing gum, a dental or oral hygiene product, a topical product, a nasal care product and a toilet article comprising the step of incorporating menthol and an effective amount of 7,8-dihydroxy-2-phenyl-4H-chromen-4-one or a salt thereof.

Another embodiment of the invention relates to a process of providing a cooling sensation in the mouth, in the nasal cavity and/or on the skin comprising the step of incorporating menthol and an effective amount of 7,8-dihydroxy-2-phenyl-4H-chromen-4-one or a salt thereof.

Another embodiment of the invention relates to a product selected from the group consisting of a foodstuff, a chewing gum, a dental or oral hygiene product, a topical product, a nasal care product and a toilet article comprising menthol and an effective amount of 7,8-dihydroxy-2-phenyl-4H-chromen-4-one or a salt thereof.

These and other embodiments of the present invention will be apparent by reading the following specification.

DETAILED DESCRIPTION OF THE INVENTION 7,8-Dihydroxy-2-phenyl-4H-chromen-4-one is sparingly soluble in aqueous solutions. Accordingly, in some embodiments, 7,8-dihydroxy-2-phenyl-4H-chromen-4-one is provided as a water-soluble salt. Salts include base addition salts which may be formed when acidic protons present are capable of reacting with inorganic or organic bases. Acceptable inorganic bases include, for example, but not limited to, sodium hydroxide, sodium carbonate, potassium hydroxide and calcium hydroxide. Acceptable organic bases include, for example, but not limited to, ethanolamine, diethanolamine, triethanolamine, tromethamine, N-methylglucamine and the like. Salts of 7,8-dihydroxy-2-phenyl-4H-chromen-4-one can be prepared by conventional methods. 7,8-Dihydroxy-2-phenyl-4H-chromen-4-one of the present invention is 7,8-dihydroxy-2-phenyl-4H-chromen-4-one, a 7,8-dihydroxy-2-phenyl-4H-chromen-4-one salt or a combination thereof 7,8-Dihydroxy-2-phenyl-4H-chromen-4-one complexes such as with cyclodextrins are also within the scope of this invention.

7,8-Dihydroxy-2-phenyl-4H-chromen-4-one is found in various plants including, for example, *Godmania aesculifolia*, *Tridax procumbens*, primula tree leaves and *Scutellaria* root (Andero, et al. (2012) *Genes, Brain and Behavio* 11 (5): 503-512; Colombo, et al. (2014) *Phytochemistry* 98: 151-159; Chan, et al. (2015) *Chemistry & Biology* 22: 355-368; Kitazaki, et al. (1996) *Papers presented at ISEC '96*, 2: 1667-1672). 7,8-Dihydroxy-2-phenyl-4H-chromen-4-one can therefore be obtained by conventional extraction methods. If provided as a botanical extract, preferably the extract is enriched for 7,8-dihydroxy-2-phenyl-4H-chromen-4-one to achieve a content of about 15% and greater, for example, from about 15% to about 95%, from about 60% to about 95% or from about 70% to about 95%. Unless otherwise specified, percentages (% s) are by weight. Further, 7,8-dihydroxy-2-phenyl-4H-chromen-4-one can be prepared from 2,3,4-trihydroxylacetophenone according to the reaction steps detailed in the Examples. Materials and catalysts were purchased from Sigma-Aldrich Chemical Company unless noted otherwise.

7,8-Dihydroxy-2-phenyl-4H-chromen-4-one is surprisingly found to have unexpected property of cooling enhancement when combined with a cooling compound, which is demonstrated to be advantageous for the use in augmenting, enhancing or imparting a cooling sensation in a product selected from the group consisting of a foodstuff, a chewing gum, a dental or oral hygiene product, a topical product, a nasal care product and a toilet article.

As used herein, a cooling compound is understood to mean a compound that provides cooling sensation. A large number of cooling compounds have been reported (See, for example, Leffingwell & Associates, Handbook of Cosmetic Science and Technology, Third Edition, Chapter 65: 661-675 (2009); http://www.leffingwell.com/cooler_than_menthol.htm (2015)). A cooling compound can be menthol, a menthol-related cooling agent, an acyclic amide, a cyclic amide or a cyclic amide with aromatic substitution. A menthol-related cooling agent can be, for example, but not limited to, menthyl methyl ether, menthyl lactate, menthyl formate, monomenthyl succinate (Cooler 1), monomenthyl glutarate (Cooler 2) or menthyl acetoacetate (Cooler 7); an acyclic amide can be, for example, but not limited to, 2-isopropyl-N,2,3-trimethylbutyramide (Cooler 3; WS-23), N-ethyl-2,2-diisopropylbutanamide (Ice 10,000), N-(2-hydroxyethyl)-2,3-dimethyl-2-isopropyl butanamide (Ice 6000) or N-(1,1-dimethyl-2-hydroxyethyl)-2,2-diethyl butanamide (Ice 11000); a cyclic amide can be, for example, but not limited to, ethyl menthane carboxamide (WS-3), N-[(ethoxycarbonyl)methyl]-p-menthane-3-carboxamide (WS-5), N-cyclopropyl-5-methyl-2-(1-methylethyl)-cyclohexanecarboxamide or menthyl pyrrolidone carboxylate (Questice); and a cyclic amide with aromatic substitution can be, for example, but not limited to, 4-[[[(2S,5R)-5-methyl-2-(1-methylethyl)cyclohexyl]carbonyl]amino]-benzeneacetamide, N-p-benzeneacetonitrile-menthanecarboxamide or N-(2-(pyridin-2-yl)ethyl)-3-p-menthanecarboxamide.

A cooling enhancer is understood to mean a compound that itself possesses no cooling property but can increase and/or extend the cooling effect of a cooling compound. The cooling enhancer of the present invention refers to 7,8-dihydroxy-2-phenyl-4H-chromen-4-one.

As used herein, the term "augmenting" in the phrase "augmenting, enhancing or imparting a cooling sensation to a product" means raising the cooling sensation of the product with an improved character. The term "enhancing" means making the cooling sensation of the product greater in effectiveness. The term "imparting" means providing the cooling sensation to the product.

As used herein, an effective amount is understood to mean the amount of 7,8-dihydroxy-2-phenyl-4H-chromen-4-one used in a cooling composition, wherein 7,8-dihydroxy-2-phenyl-4H-chromen-4-one enhances and/or extends the cooling sensation of the cooling composition in the mouth, in the nasal cavity, and/or on the skin. The effective amount may vary depending on many factors including other ingredients, their relative amounts and the cooling effect that is desired. Any amount of 7,8-dihydroxy-2-phenyl-4H-chromen-4-one that provides the desired degree of cooling enhancement without exhibiting off-taste can be used. Generally, the effective amount is greater than about 1 part per billion (ppb) by weight of the cooling composition, preferably from about 10 ppb to about 2000 parts per million (ppm), more preferably from about 100 ppb to about 1000 ppm, even more preferably from about 1 to about 100 ppm and yet even more preferably from about 10 to about 50 ppm by weight of the cooling composition.

In one embodiment, the invention provides a cooling composition containing an effective amount of 7,8-dihydroxy-2-phenyl-4H-chromen-4-one and a cooling compound in a reduced amount in order to provide the same level of cooling sensation when the cooling compound is used alone in a traditional amount. In this respect, the amount of cooling compound used in a topical or ingestible product can be reduced by at least about 10%, 20%, 30%, 40%, 50%, 60%, 70%, 80%, 90%, or 95%, from about 60% to about 99% or from about 20% to about 50%.

As used herein, a foodstuff includes both solid and liquid ingestible materials for man or animals, which materials usually do, but need not, have nutritional value. Thus, a foodstuff includes food products, such as meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like. A dental and oral hygiene product includes toothpastes, tooth gels, dental flosses, denture cleansers, denture adhesives, dentifrices, tooth whitening, mouthwashes and the like. A topical product includes topical cosmetic and topical medical products. A toilet article includes toilet water, toilet cleaners, bleach additives and the like.

When 7,8-dihydroxy-2-phenyl-4H-chromen-4-one is used in an orally consumable composition, they can be combined with conventional flavoring ingredients or adjuvants, which are well known in the art. Requirements of such flavoring ingredients and adjuvants are that: (1) they be organoleptically compatible with 7,8-dihydroxy-2-phenyl-4H-chromen-4-one whereby the flavor of the ultimate consumable composition to which 7,8-dihydroxy-2-phenyl-4H-chromen-4-one is added is not detrimentally affected by the use of such flavoring ingredients and adjuvants; and (2) they be ingestible acceptable and thus nontoxic or otherwise non-deleterious. In addition, the orally consumable composition can broadly include other flavor materials, vehicles, stabilizers, thickeners, surface active agents, conditioners, and flavor intensifiers.

Additional materials can also be used in conjunction with 7,8-dihydroxy-2-phenyl-4H-chromen-4-one to encapsulate and/or deliver the flavor enhancement. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

The following are provided as specific embodiments of the present invention. Other modifications of this invention will be readily apparent to those skilled in the art. Such modifications are understood to be within the scope of this invention. As used herein all percentages are weight percent unless otherwise noted, ppb is understood to stand for parts per billion, ppm is understood to stand for parts per million, L is understood to be liter, mL is understood to be milliliter, g is understood to be gram, mol is understood to be mole, and mmol is understood to be millimole.

Example I

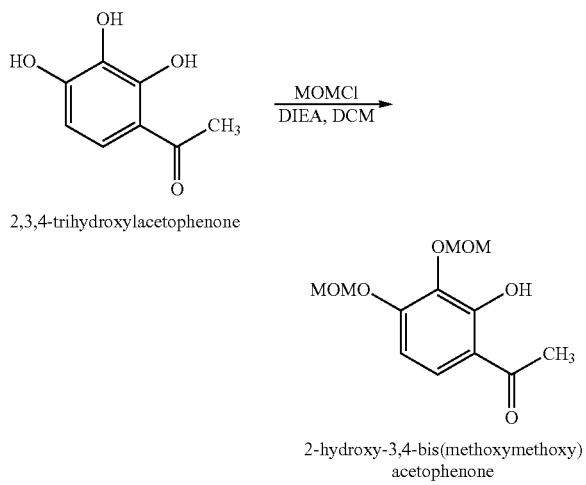

2,3,4-trihydroxylacetophenone 2-hydroxy-3,4-bis(methoxymethoxy) acetophenone

Preparation of 2-Hydroxy-3,4-bis(methoxymethoxy)acetophenone

To a solution of 2,3,4-trihydroxylacetophenone (125.0 g, 0.743 mol) and N,N-diisopropylethylamine (DIEA) (211.0 g, 1.64 mol) in dichloromethane (DCM) (2.9 L) was added dropwise methoxymethyl chloride (MOMCl) (126.6 mL, 1.64 mol) at 0-5° C. The reaction mixture was then stirred at room temperature for 2 hours. After the reaction was complete as checked by thin layer chromatography (TLC), the solution was diluted with water (2 L), and extracted twice with dichloromethane. The combined organic layers were washed with water, brine, dried over sodium sulfate ($Na_2SO_4$), filtered, and concentrated under reduced pressure. The resultant residue was purified by chromatography on silica gel eluting with ethyl acetate (EtOAc)/hexanes (15:85) to afford the title compound 2-hydroxy-3,4-bis (methoxymethoxy)acetophenone as an off-white solid (125.0 g).

$^1$H NMR (400 MHz, DMSO-$d_6$) δ: 2.60 (s, 3H), 3.41 (s, 3H), 3.51 (s, 3H), 5.07 (s, 2H), 5.33 (s, 2H), 6.76 (d, J=8.8 Hz, 1H), 7.71 (d, J=8.8 Hz, 1H), 12.61 (s, 1H). MS 257 (MH$^+$).

Example II

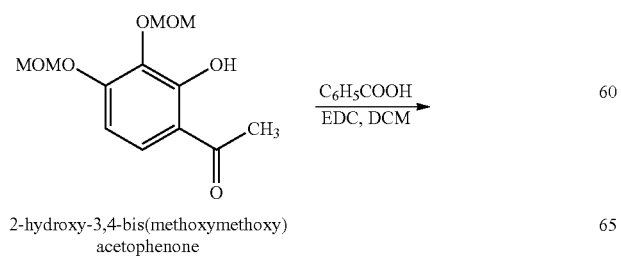

2-hydroxy-3,4-bis(methoxymethoxy) acetophenone 6-acetyl-2,3-bis(methoxymethoxy) phenyl benzoate

Preparation of 6-Acetyl-2,3-bis(methoxymethoxy)phenyl benzoate

To a solution of 2-hydroxy-3,4-bis(methoxymethoxy)acetophenone (obtained as above in EXAMPLE I) (125.0 g, 0.488 mol), benzoic acid ($C_6H_5COOH$) (89.4 g, 0.732 mol), and dimethylaminopyridine (DMAP) (6.0 g, 48.8 mmol) in dichloromethane (3.2 L) was added 1-ethyl-3-(3-dimethylaminopropyl)carbodiimide (EDC) (280.5 g, 1.463 mol) at room temperature. The solution was stirred at room temperature for overnight till the reaction was complete as indicated by TLC. The reaction mixture was quenched with water (2 L), and extracted twice with dichloromethane. The combined organic layers were washed with water, brine, dried over sodium sulfate, filtered, and concentrated under reduced pressure. The resultant residue was purified by chromatography on silica gel eluting with EtOAc/hexanes (6:4) to afford the title compound 6-acetyl-2,3-bis(methoxymethoxy)phenyl benzoate as an off-white solid (150.0 g).

$^1$H NMR (400 MHz, DMSO-$d_6$) δ: 2.47 (s, 3H), 3.33 (s, 3H), 3.44 (s, 3H), 5.07 (s, 2H), 5.38 (s, 2H), 7.22 (d, J=8.8 Hz, 1H), 7.63 (d, J=7.6 Hz, 2H), 7.74-7.80 (m, 2H), 8.13-8.16 (m, 2H). MS 361 (MH$^+$).

Example III

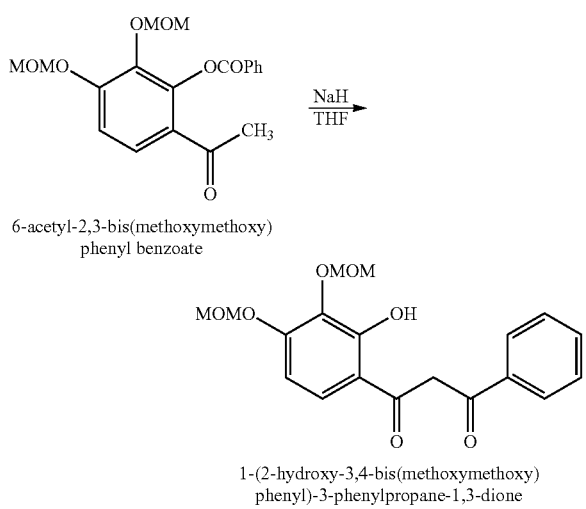

6-acetyl-2,3-bis(methoxymethoxy) phenyl benzoate 1-(2-hydroxy-3,4-bis(methoxymethoxy) phenyl)-3-phenylpropane-1,3-dione

Preparation of 1-(2-Hydroxy-3,4-bis (methoxymethoxy)phenyl)-3-phenylpropane-1,3-dione To a stirred solution of 6-acetyl-2,3-bis (methoxymethoxy)phenyl benzoate (obtained as above in EXAMPLE II) (80.0 g, 0.222 mol) in tetrahydrofuran (THF) was added in small portions sodium hydride (NaH) (60% dispersion in mineral oil, 53.28 g) at 0° C. under nitrogen. The reaction mixture was warmed up to room temperature gradually and then to 50° C. and stirred at that temperature for 1 hour. After the reaction was complete as indicated by TLC, the reaction mixture was cooled down to 0° C. and carefully quenched with water (1 L), and extracted twice with ethyl acetate. The combined organic layers were washed with water, brine, dried over sodium sulfate, filtered, and concentrated under reduced pressure. The resultant residue was triturated with diethyl ether to afford the title compound 1-(2-hydroxy-3,4-bis(methoxymethoxy)phenyl)-3-phenylpropane-1,3-dione as a pale-yellow solid (69.6 g).

$^1$H NMR (400 MHz, DMSO-d$_6$/D$_2$O) δ: 3.40-3.53 (m, 8H), 5.05-5.14 (m, 2H), 5.30-5.34 (m, 2H), 6.74-6.90 (m, 1H), 7.40-7.71 (m, 4H), 7.97-8.01 (m, 1H), 8.07-8.09 (m, 1H). MS 361 (MH$^+$).

Example IV

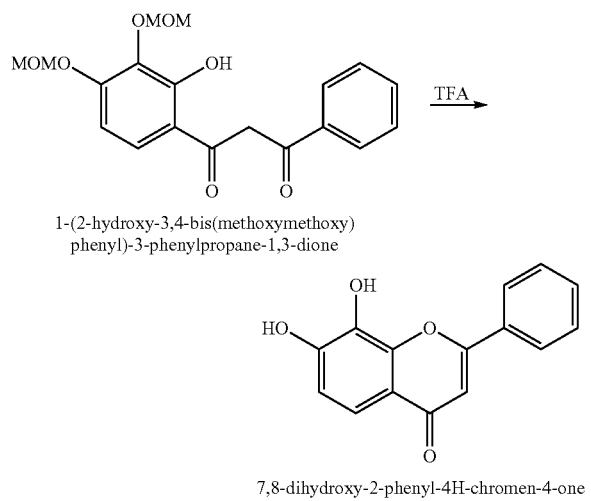

Preparation of 7,8-Dihydroxy-2-phenyl-4H-chromen-4-one (Formula I): A solution of 1-(2-hydroxy-3,4-bis(methoxymethoxy)phenyl)-3-phenylpropane-1,3-dione (obtained as above in EXAMPLE III) (65.0 g, 0.18 mol) in trifluoroacetic acid (TFA) (325 mL) was stirred at room temperature for 1 hour till the reaction was complete as indicated by TLC. The reaction mixture was then cooled down to 5-10° C., and to this solution was added water. The precipitate was collected by filtration, washed with ethyl acetate and subsequently with water, and dried under vacuum to afford the title compound 7,8-dihydroxy-2-phenyl-4H-chromen-4-one as an off-white solid (35.5 g). M.p. 202-205° C.

$^1$H NMR (400 MHz, DMSO-d$_6$) δ: 6.90 (s, 1H), 6.96 (d, J=8.8 Hz, 1H), 7.43 (d, J=8.8 Hz, 1H), 7.56-7.63 (m, 3H), 8.15-8.17 (m, 2H), 9.52 (br., 1H), 10.32 (br., 1H). MS 255 (MH$^+$).

7,8-Dihydroxy-2-phenyl-4H-chromen-4-one (Formula I) (20 ppm in water) was described as having slightly stringency and bitterness and possessing no cooling property.

Example V

The flavor compositions of menthol (35 ppm) combined with 7,8-dihydroxy-2-phenyl-4H-chromen-4-one (Formula I) at different concentrations were evaluated by a trained sensory panel. Sensory results are reported in the following.

| Composition | Concentration (ppm) (Formula I) | Flavor Profile |
|---|---|---|
| Menthol | 0 | Cooling sensation |
| Menthol/Formula I | 1 | Marginal cooling enhancement |
| Menthol/Formula I | 2 | Marginal cooling enhancement |
| Menthol/Formula I | 5 | Marginal cooling enhancement |
| Menthol/Formula I | 10 | ~10% cooling enhancement |
| Menthol/Formula I | 20 | ~20% cooling enhancement, reduced bitterness |
| Menthol/Formula I | 30 | ~20% cooling enhancement, slight burning note |
| Menthol/Formula I | 40 | Cooling enhancement, reduced bitterness and burning note |
| Menthol/Formula I | 50 | Cooling enhancement, harsh burning note |
| Menthol/Formula I | 100 | Cooling enhancement, harsh burning note |

Formula I enhanced the cooling sensation of menthol.

Example VI

The sodium salt of 7,8-dihydroxy-2-phenyl-4H-chromen-4-one on maltodextrin (Na-Formula I) was prepared and its cooling enhancement was similarly evaluated in menthol (35 ppm).

| Composition | Concentration (ppm) (Na-Formula I) | Flavor Profile |
|---|---|---|
| Menthol | 0 | Cooling sensation |
| Menthol/Na-Formula I | 1 | Marginal cooling enhancement |
| Menthol/Na-Formula I | 2 | Marginal cooling enhancement |
| Menthol/Na-Formula I | 5 | Marginal cooling enhancement |
| Menthol/Na-Formula I | 10 | ~15% cooling enhancement |
| Menthol/Na-Formula I | 20 | ~25% cooling enhancement, reduced bitterness |
| Menthol/Na-Formula I | 30 | ~25% cooling enhancement, slight burning note |
| Menthol/Na-Formula I | 40 | Cooling enhancement, reduced bitterness and burning note |
| Menthol/Na-Formula I | 50 | Cooling enhancement, harsh burning note |
| Menthol/Na-Formula I | 100 | Cooling enhancement, harsh burning note |

Na-Formula I also enhanced the cooling sensation of menthol.

Example VII

The cooling enhancement of Formula I and Na-Formula I in cooling compounds including WS-5 (30 ppm), WS-23 (35 ppm), menthyl lactate (35 ppm), WS-3 (30 ppm) and Cooler 2 (10 ppm) was also evaluated.

| Formula I (ppm) | Evaluation on the Cooling Enhancement of Formula I | | | | |
|---|---|---|---|---|---|
| | 1 | 2 | 5 | 10 | 20 |
| WS-5 (30 ppm) | Marginal enhancement | Marginal enhancement | Marginal enhancement | ~15% enhancement | ~20% enhancement |

| | | -continued | | | |
|---|---|---|---|---|---|
| WS-23 (35 ppm) | Marginal enhancement | Marginal enhancement | Marginal enhancement | ~10% enhancement | ~20% enhancement |
| Menthyl lactate (35 ppm) | Marginal enhancement | Marginal enhancement | Marginal enhancement | ~10% enhancement | ~20% enhancement |
| WS-3 (30 ppm) | Marginal enhancement | Marginal enhancement | Marginal enhancement | ~15% enhancement | ~20% enhancement |
| Cooler 2 (10 ppm) | Marginal enhancement | Marginal enhancement | Marginal enhancement | ~10% enhancement | ~10% enhancement |

| Formula I (ppm) | Evaluation on the Cooling Enhancement of Formula I | | | |
|---|---|---|---|---|
| | 30 | 40 | 50 | 100 |
| WS-5 (30 ppm) | ~20% enhancement, slight burning note | Enhancement, harsh burning note | Enhancement, harsh burning note | Enhancement, harsh burning note |
| WS-23 (35 ppm) | ~20% enhancement, slight burning note | Enhancement, harsh burning note | Enhancement, harsh burning note | Enhancement, harsh burning note |
| Menthyl lactate (35 ppm) | ~20% enhancement, slight burning note | Enhancement, harsh burning note | Enhancement, harsh burning note | Enhancement, harsh burning note |
| WS-3 (30 ppm) | ~20% enhancement, slight burning note | Enhancement, harsh burning note | Enhancement, harsh burning note | Enhancement, harsh burning note |
| Cooler 2 (10 ppm) | ~20% enhancement, slight burning note | Enhancement, harsh burning note | Enhancement, harsh burning note | Enhancement, harsh burning note |

| Na-Formula I (ppm) | Evaluation on the Cooling Enhancement of Na-Formula I | | | | |
|---|---|---|---|---|---|
| | 1 | 2 | 5 | 10 | 20 |
| WS-5 (30 ppm) | Marginal enhancement | Marginal enhancement | Marginal enhancement | ~20% enhancement | ~25% enhancement |
| WS-23 (35 ppm) | Marginal enhancement | Marginal enhancement | Marginal enhancement | ~15% enhancement | ~25% enhancement |
| Menthyl lactate (35 ppm) | Marginal enhancement | Marginal enhancement | Marginal enhancement | ~15% enhancement | ~25% enhancement |
| WS-3 (30 ppm) | Marginal enhancement | Marginal enhancement | Marginal enhancement | ~20% enhancement | ~25% enhancement |
| Cooler 2 (10 ppm) | Marginal enhancement | Marginal enhancement | Marginal enhancement | ~15% enhancement | ~15% enhancement |

| Na-Formula I (ppm) | Evaluation on the Cooling Enhancement of Na-Formula I | | | |
|---|---|---|---|---|
| | 30 | 40 | 50 | 100 |
| WS-5 (30 ppm) | ~25% enhancement, slight burning note | Enhancement, harsh burning note | Enhancement, harsh burning note | Enhancement, harsh burning note |
| WS-23 (35 ppm) | ~25% enhancement, slight burning note | Enhancement, harsh burning note | Enhancement, harsh burning note | Enhancement, harsh burning note |
| Menthyl lactate (35 ppm) | ~25% enhancement, slight burning note | Enhancement, harsh burning note | Enhancement, harsh burning note | Enhancement, harsh burning note |
| WS-3 (30 ppm) | ~25% enhancement, slight burning note | Enhancement, harsh burning note | Enhancement, harsh burning note | Enhancement, harsh burning note |
| Cooler 2 (10 ppm) | ~15% enhancement, slight burning note | Enhancement, harsh burning note | Enhancement, harsh burning note | Enhancement, harsh burning note |

Formula I and Na-Formula I enhanced the cooling sensation of various cooling compounds.

What is claimed is:

1. A cooling composition consisting of a cooling compound selected from the group consisting of menthol; menthyl methyl ether, menthyl lactate, menthyl formate, monomenthyl succinate, monomenthyl glutarate, menthyl acetoacetate; an acyclic amide; a cyclic amide; a cyclic amide with aromatic substitution; and a mixture thereof and an effective amount of 7,8-dihydroxy-2-phenyl-4H-chromen-4-one, wherein the effective amount is from about 10 to about 50 ppm by weight of the composition.

2. The cooling composition of claim 1, wherein the cooling compound is selected from the group consisting of menthol, 2-isopropyl-N,2,3-trimethylbutanamide, N-ethyl-2,2-diisopropylbutanamide, N-(2-hydroxyethyl)-2,3-dimethyl-2-isopropyl butanamide, N-(1,1-dimethyl-2-hydroxyethyl)-2,2-diethyl butanamide, ethyl menthane carboxamide, N-[(ethoxycarbonyl)methyl]-p-menthane-3-carboxamide, N-cyclopropyl-5-methyl-2-(1-methylethyl)-cyclohexanecarboxamide, menthyl pyrrolidone carboxylate, 4-[[[(2S,5R)-5-methyl-2-(1-methylethyl)cyclohexyl]carbonyl]amino]-benzeneacetamide, N-p-benzeneacetonitrile-menthanecarboxamide, N-(2-(pyridin-2-yl)ethyl)-3-p-menthanecarboxamide and a mixture thereof.

3. The cooling composition of claim 2, wherein the cooling compound is menthol.

4. A process of augmenting, enhancing or imparting a cooling sensation to a product selected from the group consisting of a foodstuff, a chewing gum, a dental or oral hygiene product, a topical product, a nasal care product and a toilet article comprising the step of incorporating the cooling composition according to claim 1.

5. The process of claim 4, wherein the cooling compound is selected from the group consisting of menthol, 2-isopropyl-N,2,3-trimethylbutyramide, N-ethyl-2,2-diisopropylbutanamide, N-(2-hydroxyethyl)-2,3-dimethyl-2-isopropyl butanamide, N-(1,1-dimethyl-2-hydroxyethyl)-2,2-diethyl butanamide, ethyl menthane carboxamide, N-[(ethoxycarbonyl)methyl]-p-menthane-3-carboxamide, N-cyclopropyl-5-methyl-2-(1-methylethyl)-cyclohexanecarboxamide, menthyl pyrrolidone carboxylate, 4-[[[(2S,5R)-5-methyl-2-(1-methylethyl)cyclohexyl]carbonyl]amino]-benzeneacetamide, N-p-benzeneacetonitrile-menthanecarboxamide, N-(2-(pyridin-2-yl)ethyl)-3-p-menthanecarboxamide and a mixture thereof.

6. The process of claim 5, wherein the cooling compound is menthol.

7. A product selected from the group consisting of a foodstuff, a chewing gum, a dental or oral hygiene product, a topical product, a nasal care product and a toilet article comprising a cooling composition, wherein the cooling composition consisting of a cooling compound selected from the group consisting of menthol; menthyl methyl ether, menthyl lactate, menthyl formate, monomenthyl succinate, monomenthyl glutarate, menthyl acetoacetate; an acyclic amide; a cyclic amide; a cyclic amide with aromatic substitution; and a mixture thereof and an effective amount of 7,8-dihydroxy-2-phenyl-4H-chromen-4-one, and wherein the effective amount is from about 10 to about 50 ppm by weight of the composition.

8. The product of claim 7, wherein the cooling compound is selected from the group consisting of menthol, 2-isopropyl-N,2,3-trimethylbutyramide, N-ethyl-2,2-diisopropylbutanamide, N-(2-hydroxyethyl)-2,3-dimethyl-2-isopropyl butanamide, N-(1,1-dimethyl-2-hydroxyethyl)-2,2-diethyl butanamide, ethyl menthane carboxamide, N-[(ethoxycarbonyl)methyl]-p-menthane-3-carboxamide, N-cyclopropyl-5-methyl-2-(1-methylethyl)-cyclohexanecarboxamide, menthyl pyrrolidone carboxylate, 4-[[[(2S,5R)-5-methyl-2-(1-methylethyl)cyclohexyl]carbonyl]amino]-benzeneacetamide, N-p-benzeneacetonitrile-menthanecarboxamide, N-(2-(pyridin-2-yl)ethyl)-3-p-menthanecarboxamide and a mixture thereof.

9. The product of claim 8, wherein the cooling compound is menthol.

10. A cooling composition consisting of a cooling compound selected from the group consisting of menthol; menthyl methyl ether, menthyl lactate, menthyl formate, monomenthyl succinate, monomenthyl glutarate, menthyl acetoacetate; an acyclic amide; a cyclic amide; a cyclic amide with aromatic substitution; and a mixture thereof; an effective amount of 7,8-dihydroxy-2-phenyl-4H-chromen-4-one; and a material selected from the group consisting of a polymer and a non-polymer, wherein the effective amount is from about 10 to about 50 ppm by weight of the composition.

11. The cooling composition of claim 10, wherein the non-polymer is selected from the group consisting of an oligomer, a surfactant, an emulsifier, a fat, a wax, a phospholipid, an organic oil, a mineral oil, a petrolatum, a natural oil, a perfume fixative, a fiber, a starch, a sugar and a solid surface material.

\* \* \* \* \*